(12) United States Patent
Altmayer et al.

(10) Patent No.: US 7,385,087 B2
(45) Date of Patent: Jun. 10, 2008

(54) METHOD FOR PRODUCING A-(3-ARYLTHIO)-ACETOPHENONES

(75) Inventors: Marco Altmayer, Ilvesheim (DE); Wolfgang Siegel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 456 days.

(21) Appl. No.: 10/547,342

(22) PCT Filed: Feb. 20, 2004

(86) PCT No.: PCT/EP2004/001676

§ 371 (c)(1),
(2), (4) Date: Sep. 1, 2005

(87) PCT Pub. No.: WO2004/078705

PCT Pub. Date: Sep. 16, 2004

(65) Prior Publication Data

US 2006/0178537 A1   Aug. 10, 2006

(30) Foreign Application Priority Data

Mar. 6, 2003   (DE) ............................... 103 09 645

(51) Int. Cl.
*C07C 319/00* (2006.01)
*C07C 321/00* (2006.01)
*C07C 323/00* (2006.01)
*C07C 381/00* (2006.01)

(52) U.S. Cl. ...................................................... 568/43

(58) Field of Classification Search .................. 568/43
See application file for complete search history.

(56) References Cited

U.S. PATENT DOCUMENTS

| 4,075,227 A | 2/1978 | Jones et al. |
| 5,710,341 A | 1/1998 | Siegel et al. |

FOREIGN PATENT DOCUMENTS

| CN | 1370533 | * | 9/2002 |
| EP | 0 735 016 | | 10/1996 |
| FR | 2 329 270 | | 10/1975 |
| WO | WO 02/42261 | | 5/2002 |
| WO | WO 03/010156 | | 2/2003 |

OTHER PUBLICATIONS

Weng et al., Improved synthesis of 4'-methoxy-2-(3-methoxyphenylthio)acetophenone, Huaxi Yaoxue Zazhi (2000), 15(6), 437,440.*

S. Kil, et al, Tetrahednon Letters, Eelsevier Science Publishers, Amsterdam, vol. 40, 1999.p. 2909-2912.

C. J. Jones, et al. F. Med. Chem., ACS, vol. 27, No. 8, pp. 1057-1066.

P. R . Olivato et al., Magn. Reson. Chem., vol. 25, 1987, pp. 179-180.

* cited by examiner

*Primary Examiner*—Yvonne (Bonnie) Eyler
*Assistant Examiner*—Chukuma O. Nwaonicha
(74) *Attorney, Agent, or Firm*—Connolly Bove Lodge & Hutz LLP

(57) ABSTRACT

A process for preparing α-(3-arylthio)acetophenones of the general formula I

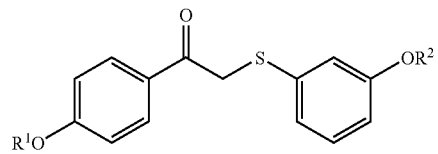

where the substituents $R^1$ and $R^2$ are each independently $C_1$-$C_6$-alkyl or an optionally substituted phenyl or benzyl radical, which comprises
A) reacting acetophenones of the general formula II where the substituent $R^1$ is as defined above

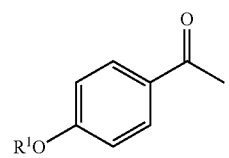

with sulfuryl chloride and subsequently hydrolyzing, and
B) reacting the reaction mixture obtained in this way with a thiophenol of the general formula III where the substituent $R^2$ is as defined above

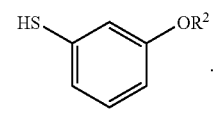

11 Claims, No Drawings

METHOD FOR PRODUCING A-(3-ARYLTHIO)-ACETOPHENONES

CROSS REFERENCE TO RELATED APPLICATION

The present application is a national stage of PCT/EP2004/001676, filed Feb. 20, 2004, which claims priority from German Patent Application No.: 103 09 645.0 filed Mar. 6, 2003.

The present invention relates to an improved process for preparing α-(3-arylthio)-acetophenones of the general formula I

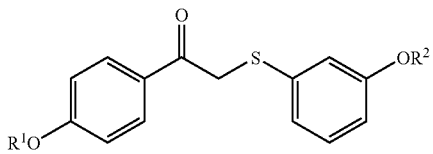

where the substituents $R^1$ and $R^2$ are each independently $C_1$-$C_6$-alkyl or an optionally substituted phenyl or benzyl radical.

The compounds of the formula I are intermediates in the synthesis of pharmaceutically active substances; 1-(4-methoxyphenyl)-2-[(3-methoxyphenyl)thio]ethanone is a building block for preparing the anti-osteoporosis active ingredient raloxifen.

The preparation of compounds of the formula I is disclosed, inter alia, by WO 02/42261. According to this teaching, α-chloro- or α-bromoacetophenones are prepared from the corresponding acetophenone and a halogenating agent, and isolated. Subsequently, they are reacted in a water-immiscible solvent with the appropriate thiophenol in alkaline aqueous solution to nucleophilically substitute the halogen atom by the thiolate anion.

However, this procedure has the disadvantage that the α-chloro or α-bromo compounds have to be isolated. This leads firstly to not inconsiderable yield losses in the workup of the reaction mixture and also in the subsequent product of value purification. Secondly, the isolation on the industrial scale is costly and inconvenient, since the compounds are strongly lacrimatory and also sensitizing, and therefore have to be transferred in a contamination-free manner.

It is an object of the present invention to find a process for preparing compounds of the general formula I which dispenses with the isolation, purification, drying and transferring of α-chloro- or α-bromoacetophenones.

We have found that this object is achieved by the process described at the outset, which comprises
A) reacting acetophenones of the general formula II where the substituent $R^1$ is as defined above

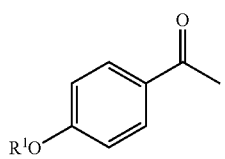

with sulfuryl chloride and subsequently hydrolyzing, and

B) reacting the reaction mixture obtained in this way with a thiophenol of the general formula III where the substituent $R^2$ is as defined above

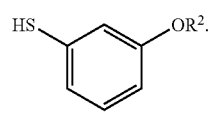

The process according to the invention serves to prepare compounds of the formula I, preferably 1-(4-methoxyphenyl)-2-[(3-methoxyphenyl)thio]ethanone.

Useful starting compounds are acetophenones of the general formula II where the substituent $R^1$ is $C_1$-$C_6$-alkyl such as methyl, ethyl, isopropyl, n-butyl or isobutyl, phenyl or benzyl, and the phenyl and benzyl radicals may bear substituents which are inert under the reaction conditions, for example halogen or oxyalkyl. Preference is given for $R^1$ to short-chain alkyl radicals, in particular methyl.

The acetophenone of the general formula II is reacted in reaction step A) with sulfuryl chloride $SO_2Cl_2$. In this reaction, a molar excess of sulfuryl chloride is generally used, preferably from 1.1 to 2 mol of sulfuryl chloride per mole of acetophenone, more preferably from 1.7 to 1.8 mol per mole.

Preference is given to carrying out the chlorination in the presence of an aliphatic alcohol. Preference is given to saturated, unbranched or branched-chain alcohols, in particular those having from one to ten carbon atoms, particularly methanol, ethanol, 1-propanol, 2-propanol, 1-butanol and 2-butanol.

The alcohols can be used in the process either as an individual substance or as a mixture.

The aliphatic alcohols are generally used in amounts of from 0.1 to 10 mol, preferably from 2 to 6 mol, per mole of acetophenone of the general formula II.

Useful additional solvents are inert organic solvents, such as saturated aliphatic hydrocarbons, for example hexane, heptane or octane, and also cycloaliphatic hydrocarbons such as cyclohexane. In addition, chlorinated aliphatic hydrocarbons, for example methylene chloride, chloroform, tetrachloromethane, can be used. It is also possible to use aromatic solvents such as benzene, toluene, ethylbenzene, xylenes such as o-xylene, haloaromatics such as chlorobenzene and dichlorobenzenes.

Preference is given to a solvent mixture of an aromatic solvent, preferably toluene, and an aliphatic alcohol such as methanol, ethanol, 2-propanol and 1-butanol, preferably 1-butanol. An excess by weight of the alcohol is advantageous, and mixing ratios of 1 part by weight of the aromatic solvent to from 2 to 20, preferably from 8 to 12, parts by weight of the aliphatic alcohol have proven particularly useful.

The acetophenone of the general formula II is customarily initially charged in this solvent or solvent mixture and sulfuryl chloride is added. The reaction can be carried out, for example, in a stirred tank. The reaction can be carried out at atmospheric pressure and a temperature of from 0 to 50° C.; at higher temperatures, the selectivity of the reaction falls, and lower temperatures afford no significant advantages with regard to selectivity, yield and process technology.

After adding the sulfuryl chloride, the mixture can continue to be stirred for a while. The reaction mixture is subsequently hydrolyzed until excess sulfuryl chloride has reacted. In a preferred implementation variant, the mixture is made weakly acidic after the hydrolysis, and the pH is adjusted to from 5.0 to 6.0. This is effected by adding bases such as sodium carbonate, calcium hydroxide, potassium hydroxide or preferably sodium hydroxide.

In reaction step B), the α-chloroacetophenone prepared in situ in reaction step A) is reacted with a thiophenol of the formula III in which the substituent $R^2$ is $C_1$-$C_6$-alkyl such as methyl, ethyl, isopropyl, n-butyl or isobutyl, phenyl or benzyl, and the phenyl and benzyl radicals may bear substituents which are inert under the reaction conditions, for example halogen or oxyalkyl. Preference is given for $R^2$ to short-chain alkyl radicals, in particular methyl.

The thiophenol of the formula III is added to the reaction mixture from step A). The amount of thiophenol is generally from 0.8 to 2.0 mol of thiophenol per mole of acetophenone of the formula II, preferably from 0.90 to 1.05 mol per mole.

In a preferred embodiment, the pH is adjusted after the addition of the thiophenol of the general formula III to from 6.0 to 9.0, for which bases such as sodium carbonate, calcium hydroxide, potassium hydroxide or preferably sodium hydroxide can be used.

The end of the reaction can be checked by means of gas chromatography.

The reaction product can be isolated in a manner known per se. To this end, the reaction mixture is preferably cooled to from 0 to 5° C., seeded with product crystals and stirred for a further approx. 30 minutes. The product is filtered, digested with water and subsequently with methanol, washed and dried.

The process according to the invention enables the preparation of α-(3-arylthio)-acetophenones of the general formula I in good yield with high purity. The disadvantages of the prior art are avoided in a manner which is unexpectedly simple from a process engineering point of view, and in particular the complicated measures for avoiding contact with the intermediates can be considerably reduced.

EXAMPLE 1

Preparation of 1-(4-methoxyphenyl)-2-[(3-methoxyphenyl)thio]ethanone 48.1 g (0.32 mol) of 4-methoxyacetophenone were initially charged in 11 ml of toluene and 117 ml of 1-butanol. With ice cooling, 74.62 g (0.55 mol) of sulfuryl chloride (acetophenone:sulfuryl chloride molar ratio 1:1.7) were added dropwise at 25-30° C. After continuing to stir for 30 minutes, the reaction mixture was hydrolyzed with 210 ml of water and adjusted to a pH of 6.0 using 40 ml of conc. sodium hydroxide solution, without the temperature exceeding 30° C.

44.80 g (0.32 mol) of 3-methoxythiophenol were then added and the pH was adjusted to 8.5 using conc. sodium hydroxide solution. After continuing to stir for 1 h, the mixture was cooled to 0-5° C., seeded with product crystals and stirred for a further 30 minutes. The crystals were filtered off, digested with 200 ml of water, then washed with 200 ml of water, digested with 75 ml of methanol and washed with 75 ml of methanol. The crystals were dried at 30° C.

Yield: 64.8 g (0.225 mol) of 1-(4-methoxyphenyl)-2-[(3-methoxyphenyl)thio]ethanone, 70% Purity (GC): 99.5%

EXAMPLE 2

Preparation of 1-(4-methoxyphenyl)-2-[(3-methoxyphenyl)thio]ethanone 48.1 g (0.32 mol) of 4-methoxyacetophenone were initially charged in 11 ml of toluene and 117 ml of 1-butanol. With ice cooling, 74.62 g (0.55 mol) of sulfuryl chloride (acetophenone:sulfuryl chloride molar ratio 1:1.7) were added dropwise at 25-30° C. After continuing to stir for 30 minutes, the reaction mixture was hydrolyzed with 210 ml of water and adjusted to a pH of 6.0 using 40 ml of conc. sodium hydroxide solution, without the temperature exceeding 30° C.

44.80 g (0.32 mol) of 3-methoxythiophenol were then added and the pH was adjusted to 7.0 using conc. sodium hydroxide solution. After continuing to stir for 1 h, the mixture was cooled to 0-5° C., seeded with product crystals and stirred for a further 30 minutes. The crystals were filtered off, digested with 200 ml of water, then washed with 200 ml of water, digested with 75 ml of methanol and washed with 75 ml of methanol. The crystals were dried at 30° C.

Yield: 63.6 g (0.221 mol) of 1-(4-methoxyphenyl)-2-[(3-methoxyphenyl)thio]ethanone, 69% Purity (GC): 97.5%

We claim:

1. A process for preparing α-(3-arylthio)acetophenones of the general formula I

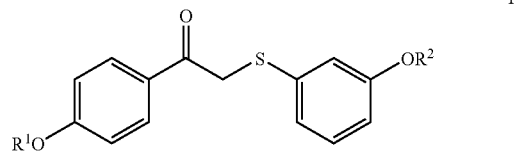

where the substituents $R^1$ and $R^2$ are each independently $C_1$-$C_6$-alkyl or an optionally substituted phenyl or benzyl radical, which comprises A) reacting acetophenones of the general formula II where the substituent $R^1$ is as defined above

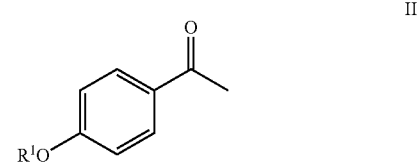

with sulfuryl chloride and subsequently hydrolyzing, and

B) reacting the reaction mixture obtained in this way with a thiophenol of the general formula III where the substituent $R^2$ is as defined above

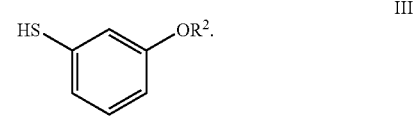

2. The process as claimed in claim 1, wherein 1-(4-methoxyphenyl)-2-[(3-methoxyphenyl)thio]ethanone is prepared.

3. A The process as claimed in claim 1, wherein reaction step A) is carried out in a solvent mixture of an aromatic solvent and an aliphatic alcohol.

4. The process as claimed in claims 1, wherein the pH is adjusted to from 5.0 to 6.0 after the hydrolysis and before the addition of the thiophenol of the general formula III.

5. The process as claimed in claims 1, wherein reaction step B) is carried out at a pH of from 6.0 to 9.0.

6. The process as claimed in claim 2, wherein reaction step A) is carried out in a solvent mixture of an aromatic solvent and an aliphatic alcohol.

7. The process as claimed in claim 2, wherein the pH is adjusted to from 5.0 to 6.0 after the hydrolysis and before the addition of the thiophenol of the general formula III.

8. The process as claimed in claim 3, wherein the pH is adjusted to from 5.0 to 6.0 after the hydrolysis and before the addition of the thiophenol of the general formula III.

9. The process as claimed in claim 2, wherein reaction step B) is carried out at a pH of from 6.0 to 9.0.

10. The process as claimed in claim 3, wherein reaction step B) is carried out at a pH of from 6.0 to 9.0.

11. The process as claimed in claim 4, wherein reaction step B) is carried out at a pH of from 6.0 to 9.0.

* * * * *